United States Patent
Scott

(10) Patent No.: US 6,183,758 B1
(45) Date of Patent: Feb. 6, 2001

(54) PHYTOCHEMICALS, NUTRIENTS & MEDICATION ABSORPTION &/OR TREATMENT

(75) Inventor: Kenneth Duane Scott, Scotts Mills, OR (US)

(73) Assignee: Highland Laboratories, Inc., Mt. Angel, OR (US)

(*) Notice: Under 35 U.S.C. 154(b), the term of this patent shall be extended for 0 days.

(21) Appl. No.: 09/015,351

(22) Filed: Jan. 29, 1998

(51) Int. Cl.[7] ................ A61K 31/74; A61K 6/00; A61K 7/00
(52) U.S. Cl. ................... 424/401; 514/844; 514/944
(58) Field of Search .................. 424/78.02, 78.03, 424/401; 514/937, 944, 946, 947, 844

(56) References Cited

U.S. PATENT DOCUMENTS 4,477,469 * 10/1984 Herschler ..................... 424/322
5,874,074 * 2/1999 Smith ........................... 424/78.02

OTHER PUBLICATIONS

Article entitled "Skin Penetration Enhancers Cited in the Technical Literature" from Pharmaceutical Technology, Nov., 1997.
Article entitled "Advances in Drug Delivery" from Pharmaceutical Technology, Jan., 1998.
"Percutaneous Absorption" from 14th Ed. Remington's Pharmaceutical Science.

* cited by examiner

Primary Examiner—Thurman K. Page
Assistant Examiner—S. Howard
(74) Attorney, Agent, or Firm—Robert L. Harrington

(57) ABSTRACT

A skin absorbent cream including the ingredients MSM, urea, propylene glycol and a large molecular medication. This combination of ingredients softens the skin to allow penetration of the medication through the skin and into the underlying blood vessels. The large molecular medication dissolves in the propylene glycol between as low as 25° C. to 150° C. and becomes the transporter through the outer skin layer and into the blood stream.

8 Claims, 1 Drawing Sheet

PHYTOCHEMICALS, NUTRIENTS & MEDICATION ABSORPTION &/OR TREATMENT

FIELD OF THE INVENTION

This invention relates to the phytochemical, nutrient & medication for improved structure, function &/or treatment of specific conditions in humans and animals through the process of skin penetration, and more particularly it relates to a skin ointment with improved skin penetration properties.

BACKGROUND OF THE INVENTION

Phytochemicals, nutrients & medications intended for transmission via the blood stream are typically entered into a person's blood stream through oral ingestion or syringe injection. An alternative form of treatment is the application of the phytochemicals, nutrients or medications to the skin with the medication being absorbed through the skin into the blood vessels underlying the epidermis part of the skin.

There are advantages of the skin application technique, i.e. the compounds can be applied to the place of the needed improvement of the structure, function or ailment and absorption into the blood vessels surrounding this condition provides a more direct and often a more effective treatment/repair of the structure, function or ailment. The problem with the technique is achieving penetration of the skin and specifically the stratum corneum area of the skin.

The compounds themselves are often not skin absorbable (evidence shows the only possible exceptions to this are sodium ions and water) and must be dissolved into a carrier or transport solution. There are solutions that can be made to be somewhat skin absorbent, especially when they are applied and then covered with a barrier such as plastic (example is Dow's Saran wrap) and this causes water to travel in and out of this upper layer of skin. This system is limited to "patches" already prepared, is expensive and limits the amount of ingredient that can be applied and the physical area that the plastic patch can be applied. Solvents are known that will achieve this in the presence of a "patch" but they must be at a precise ratio of ingredient to the solvent (near saturation point). Known solutions that are acceptable for topical application and used without a "patch" are either not sufficiently absorbable into the skin or not sufficiently solvent, e.g., if the ingredient is one having large molecules, the solution does not readily dissolve the medication.

SUMMARY OF THE INVENTION

The present invention involves the combination of two separate and seemingly unrelated solutions. The first solution has a makeup of water, methyl sulfonyl methane (MSM—the oxide form of DMSO) and urea. MSM & urea in combination produce some but no significant penetration of the skin and they do not dissolve the large molecules often found in phytochemicals (active plant compounds), organic nutrients or prescribed medications. The combination of MSM and urea, used topically, is itself patented (U.S. Pat. No. 4,477,469) and has a number of benefits. One not so well known or appreciated is its ability not only to "soften" the skin but actually open the "horny layer" (stratum corneum, stratum lucidum & stratum granulosum) to allow penetration of water and organic solvents such as propylene glycol.

The second solution includes as one of the ingredients propylene glycol. Propylene glycol is recognized as being beneficial for skin penetration and it dissolves large molecules, e.g., at temperatures of between about 25° and 150° C. However, in the past to get the large organic molecules to pass the horny layer and be released one had to use a minimum amount of propylene glycol to solublize the compound and cover the area with the before mentioned "patch". In this current invention it has been found that the before mentioned limits do not apply. Therefore with this second solution the desired ingredient (phytochemical, nutrient or medication) is dissolved in the propylene glycol completely and without being at the saturation point.

Upon mixing the two solutions, the mixture surprisingly produces rapid penetration of the ingredient through the skin tissue (epidermis) and into the blood vessels underlying the skin tissue (the dermis & subcutaneous tissues). It is theorized that the MSM & urea, although only a mediocre skin penetration, expands the platelets of the skin particularly in the horny layer of the skin. The expansion of the platelets opens the interstices and enables the rapid penetration of the propylene glycol solution, i.e., containing the active compound (phytochemical, nutrient or medication).

The invention will be more fully appreciated upon reference to the following detailed description of a preferred embodiment of the invention having reference to the accompanying drawings.

DESCRIPTION OF THE PREFERRED EMBODIMENT

Figure 1:
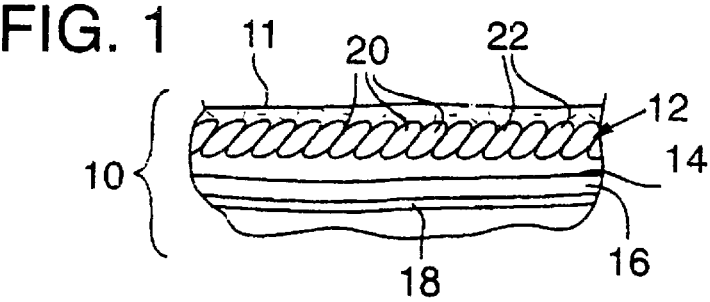
FIG. 1 is a schematic illustration of human skin.

The present invention relates to the medicinal, structure or function treatment of a human or animal. Illustrated is a person's skin layer 10. It will be understood that the invention here is transportation of the medication, nutrient or phytochemical into a person's blood stream through the skin tissue. There are many conditions, some that are localized and will be more directly benefitted by the invention herein but others that are not localized which nevertheless will benefit from the medication, nutrient or phytochemical introduced into the blood stream. The invention provides the form of delivery which is here referred to as skin absorption.

Oral injection is a common alternative form but is not always desirable to the individual and the beneficial effects are slower and the gastrointestinal tract may either inhibit or destroy certain compounds.

Syringe induction is a further alternative form and produces quick results but is often not desirable to the individual.

Patch absorption is limited in active ingredient and due to its nature is not always desirable and can have poor individual acceptance.

Skin injection through topical application is the least objectionable but the skin is a very effective barrier to many compounds (other than sodium and water). A typical skin injection technique is to dissolve the compound to be used in a liquid transporter or carrier that has the capability of penetrating or being absorbed by the skin. The process has not gained wide acceptance for a number of reasons. In some instances there is a concern for side affects from the transporting substance which is also injected into the blood stream. Some transporting substances (such as the Nicotinate salts) have low patient acceptance due to the skin irritation caused, others may cause other unacceptable side effects. Of those known to be safe, their absorbent properties are not effectively adequate and/or they do not dissolve the large molecular compounds contemplated by the present invention.

Two substances which fit the category of being marginal absorbents are MSM and urea (in combination) and propylene glycol. MSM and urea (in combination) is used for a number of different types of medicinal and nutrient application (internally and topically—see U.S. Pat. No. 4,477,469). As a topical (skin applied) ointment, the MSM-urea is believed to prevent cross-linking so as to slow the effects of UV light (sunlight) and thus impedes the aging of skin. It can be observed to soften the skin. Experiments have shown that the MSM-urea blend will absorb into the outer layer of the skin but not sufficiently to function as an effective medicinal or nutrient carrier or transporter.

Propylene glycol is an excellent absorber of large molecular compounds, e.g., of steroid type medication. However, propylene glycol, like MSM-urea, will absorb into the skin but again not, by itself, sufficiently to function as an effective medicinal or nutrient carrier. The combination of MSM-urea and propylene glycol might be expected to produce an ointment that dissolves large molecular medications, phytochemicals or nutrients and inhibit cross-linking, but would not be expected to produce an effective absorbent of these compounds.

This combination nevertheless does produce an excellent transporter of large molecular medications (e.g., steroids & alkaloids). It is theorized that the major inhibitor to the absorption of propylene glycol is the horny outer layers of skin. It is further theorized that the MSM-urea functions to swell or expand the platelets in this outer horny skin layer which opens the interstices between the platelets. This facilitates the transportation of the propylene glycol (and the medication, phytochemical or nutrient dissolved therein) through this outer layer and thus enabling the rapid transportation of the medication into the blood stream.

The procedure just described is illustrated in FIG. 1. Reference number 10 refers to the skin and the layers of skin including the horny outer layer (stratum corneum) 12 and the underlying layers (stratum lucidum and stratum granulosum) sometimes referred to as the true skin layer 14 and the adipose tissue layer (including the dermis and subcutaneous tissue) 16. Imbedded in the adipose layer and the dermis layer are the blood vessels 18. As will be noted, the horny outer shell is indicated to be made of overlapping platelets 20 and swelling of the platelets is believed to open interstices 22 between the platelets 20.

Regardless, the combination has produced an excellent topical ointment for transportation of large molecular phytochemicals, nutrients and medications through the skin 10 and into the underlying blood vessels 18.

Figure 2A:
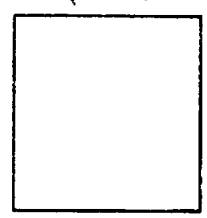
FIGS. 2A–2D are schematic illustrations of a process used for producing an ointment of the present invention.

FIGS. 2A–2D schematically illustrate the process for producing a topical ointment in accordance with the invention. In FIG. 2A, there is first mixed the materials of the MSM and urea with purified water. This is described in detail in U.S. Pat. No. 4,477,469 and the disclosure thereof is incorporated herein by reference. MSM is available from Vita-Flex Nutrition, P.O. Box 070140, Staten Island, N.Y. 10307-0140 or Carolwood Corporation, 305 Third St., Greenville, Pa. 16125. Urea and propylene glycol (cosmetic grades) are available from numerous sources in the U.S.A. and as such should cause no problem locating adequate supply.

Figure 2B:
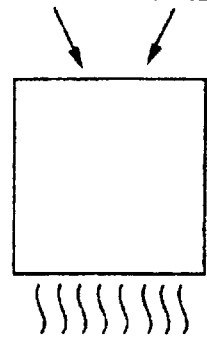
Figure 2C:
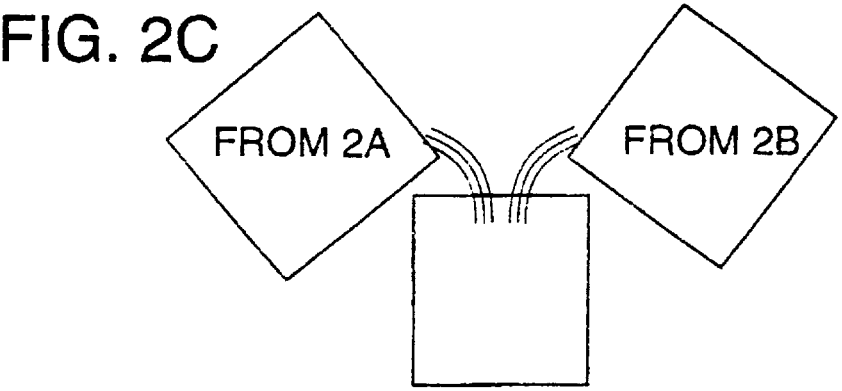
Figure 2D:
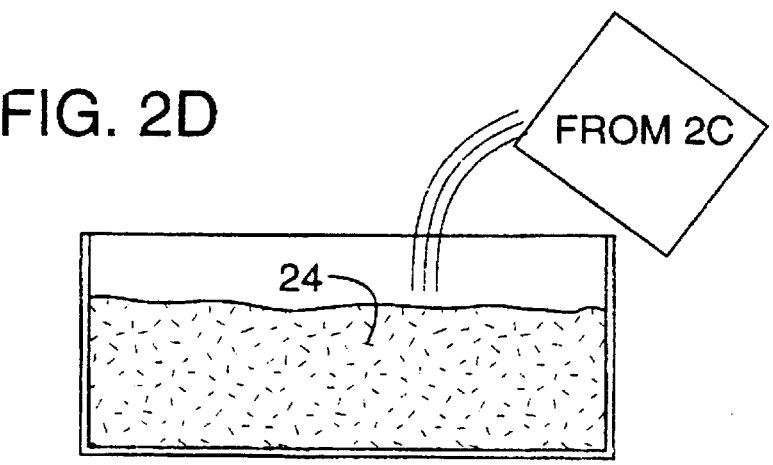

The mixture of propylene glycol and any large molecular compounds (phytochemicals, nutrients or medication) is illustrated in FIG. 2B. The propylene glycol is heated to about 120° C. and the active ingredient (phytochemical, nutrient or medication) is added. FIG. 2C represents the inter-mixture of the MSM-urea solution and propylene glycol solution (with the dissolved ingredient) and FIG. 2D represents the mixture of FIG. 2C added to an emulsion or gel 24, e.g., any of a number of creamy or gel substances prepared for topical application including ointments and salves. The general category of skin creams (or gels) are considered desirable as they are widely used and accepted for skin health and beautification.

Whereas the above description is considered to adequately teach a person skilled in this art how to produce the product of the invention, the following is a detailed example of the ingredients and procedures.

EXAMPLE

Formulation For Manufacture

| Ingredients | Amount |
| --- | --- |
| FACE CREAM BASE | 587.76 GM |
| GLYCERIN | 10.00 GM |
| VIT E LIQ 1000 IN GRAM | 10.00 GM |
| WATER (Deionized) | 99.00 GM |
| PROPYLENE GLYCOL | 100.00 GM |
| PROGESTERONE POWDER | 19.00 GM |
| UREA | 100.00 GM |
| MSM | 70.00 GM |
| FRAGRANCE | 4.00 GM |
| CITRIC ACID | 0.25 GM |

The process used to produce the topical ointment from these ingredients involves (a) heating a mixture of the Vitamin E and glycol to 120 C., (b) add the progesterone to the mixture, (c) cool the above to 85° C. and blend it into the cosmetic base cream which is previously warmed to 40° C., (d) add the urea and MSM previously dissolved in most of the water (heated), (e) the citric acid is dissolved in the remaining water and cooled to 28° C. or less (stir every 20 minutes), and (f) blend the citric acid solution and the citrus fragrance into the base cream mixture and check the acidic (pH) reading to assure that it is between 5.0 and 5.4.

The above disclosures are by way of example only and those skilled in the art will appreciate that the invention can be produced in numerous variations and forms. Accordingly, the invention is not limited by the disclosures but rather is defined by the claims appended hereto.

What is claimed is:

1. A composition for penetrating through the skin to underlying blood vessels consisting essentially of methyl sulfonyl methane urea, propylene glycol and an organic compound having structure, function or medicinal properties.

2. A composition for penetrating through the skin and into underlying blood vessels consisting essentially of:
   (a) a mixture of methly sulfonyl methane and urea dissolved in purified water;
   (b) a mixture of a quantity of propylene glycol and a quantity of an organic compound having structure, function or medicinal properties dissolved in the propylene glycol; and
   (c) said mixture of compound (a) blended with said mixture of compound (b).

3. An emulsion or gel that forms a base cream or gel and the composition of claim 1 mixed into the base cream or gel to form a medicinal, structure or function cream or gel.

4. A composition as defined in claim 2 wherein substantially equal parts plus or minus 50% of propylene glycol, urea, and methyl sulfonyl methane are mixed with a quantity of the organic compound totally dissolved in the propylene glycol, the organic compound being about 20% of the propylene glycol.

5. A composition as defined in claim 2 wherein the large molecular organic compound is either a steroid, alkaloid or nutrient.

6. A process for producing a composition for penetrating through the skin and into the blood vessels which consisting essentially of:

(a) producing a dissolved mixture of urea and methyl sulfonyl methane;

(b) producing a dissolved mixture of propylene glycol with a large molecular organic substance; and (c) inter-mixing ingredients (a) and (b).

7. A process as defined in claim 6 wherein the propylene glycol is heated to a temperature between 25° C. and 150° C. and completely dissolving the organic substance therein prior to inter-mixing with the dissolved compound in step (a).

8. A process for producing skin penetrating medicinal treatment or to assist in the structure or function substance which includes:

producing an emulsion or a gel suitable as a skin cream or gel and adding thereto the substance of claim 7.

* * * * *